United States Patent
Navon et al.

(10) Patent No.: US 9,655,859 B2
(45) Date of Patent: May 23, 2017

(54) ACCORDION PILL COMPRISING LEVODOPA FOR AN IMPROVED TREATMENT OF PARKINSON'S DISEASE SYMPTOMS

(71) Applicant: INTEC PHARMA LTD., Jerusalem (IL)

(72) Inventors: Nadav Navon, Jerusalem (IL); David Kirmayer, Jerusalem (IL); Julia Shvetz, Jerusalem (IL); Elena Kluev, Jerusalem (IL); Eva Abramov, Jerusalem (IL); Zeev Weiss, Jerusalem (IL); Giora Carni, Jerusalem (IL)

(73) Assignee: INTEC PHARMA LTD., Jerusalem (IL)

( * ) Notice: Subject to any disclaimer, the term of this patent is extended or adjusted under 35 U.S.C. 154(b) by 0 days.

(21) Appl. No.: 15/014,854

(22) Filed: Feb. 3, 2016

(65) Prior Publication Data
US 2016/0220495 A1 Aug. 4, 2016
US 2017/0087091 A9 Mar. 30, 2017

Related U.S. Application Data

(63) Continuation of application No. 13/882,768, filed as application No. PCT/IB2011/002888 on Nov. 1, 2011, now abandoned.

(60) Provisional application No. 61/408,985, filed on Nov. 1, 2010.

(51) Int. Cl.
| | |
|---|---|
| *A61K 9/48* | (2006.01) |
| *A61K 9/00* | (2006.01) |
| *A61K 9/70* | (2006.01) |
| *A61K 31/198* | (2006.01) |

(52) U.S. Cl.
CPC .......... *A61K 9/4808* (2013.01); *A61K 9/0065* (2013.01); *A61K 9/7007* (2013.01); *A61K 31/198* (2013.01)

(58) Field of Classification Search
None
See application file for complete search history.

(56) References Cited

U.S. PATENT DOCUMENTS

| | | | | |
|---|---|---|---|---|
| 8,771,730 B2* | 7/2014 | Navon | ................. | A61K 9/2886 424/451 |
| 9,072,663 B2* | 7/2015 | Navon | ................. | A61K 9/2886 |
| 9,259,387 B2* | 2/2016 | Navon | ................. | A61K 9/2886 |
| 2004/0092544 A1* | 5/2004 | Horowski | .............. | A61K 31/48 514/288 |
| 2005/0163850 A1* | 7/2005 | Wong | ................... | A61K 9/0004 424/473 |
| 2007/0178149 A1* | 8/2007 | Flashner-Barak | ... | A61K 9/1635 424/458 |
| 2010/0196463 A1 | 8/2010 | Quik | | |

FOREIGN PATENT DOCUMENTS

| | | |
|---|---|---|
| WO | 2009144558 A1 | 12/2009 |
| WO | 2010019915 A1 | 2/2010 |

OTHER PUBLICATIONS

Goetz et al. "Movement Disorder Society-Sponsored Revision of the Unified Parkinson's Disease Rating Scale (MDS-JPSRD): Process, Format, and Clinimetric Testing Plan" Movement Disorders. 22.1:41-47 (2007).

* cited by examiner

*Primary Examiner* — Hasan Ahmed
(74) *Attorney, Agent, or Firm* — Browdy and Neimark, PLLC

(57) ABSTRACT

The invention provides for the use of an accordion pill comprising levodopa for the treatment of symptoms of Parkinson's disease in a subject in need thereof over a 24 hour period, to be administered to the subject in a twice daily administration regimen, with an interval of about 8 to about 1 0 hours between the first dose and the second dose, and with an interval of about 14 to about 16 hours between the second dose and the first dose of the following day. The twice daily administration regimen provides a stable blood plasma level of levodopa in the subject after multiple administrations and is effective in treating the symptoms of Parkinson's disease over a 24 hour period.

18 Claims, 5 Drawing Sheets

AP-CD/LD 250 mg - levodopa pharmacokinetics in early stage PD patients (N=12)

AP-CD/LD 375 mg - levodopa pharmacokinetics in advanced PD patients (N=8)

AP-CD/LD 50/500 mg - levodopa pharmacokinetics healthy volunteers (N=18)

Levodopa absorption profile as percentage of total bioavailable dose, derived from data of the example 2.

Strong correlation between steady LD blood plasma levels and elevated UPDRS scores of the patients – AP-CD/LD – 50/375 mg

ACCORDION PILL COMPRISING LEVODOPA FOR AN IMPROVED TREATMENT OF PARKINSON'S DISEASE SYMPTOMS

CROSS REFERENCE TO RELATED APPLICATIONS

This application is a 35 U.S.C. §371 National Phase Entry Application of International Application No. PCT/IB2011/002888 filed on Nov. 1, 2011, which designates the U.S., and which claims benefit of 35 U.S.C. §119(e) of U.S. Provisional Application No. 61/408,985 filed on Nov. 1, 2010, the contents of which are incorporated herein by reference in their entireties.

FIELD OF THE INVENTION

The present invention relates to the use of multi-layered, biodegradable, gastroretentive drug formulations, known as the Accordion Pill, for the controlled release of carbidopa/levodopa in an improved method of treatment of Parkinson's Disease symptoms.

BACKGROUND OF THE INVENTION

Levodopa (LD) is the most effective drug for the symptomatic treatment of Parkinson's disease (PD). No other medical or surgical therapy currently available has been shown to provide anti-Parkinson benefits superior to what can be achieved with LD. However, following few years of LD treatment, the actions of each dose tend to wear off in the majority of PD patients. This wearing off between doses is strongly correlated to the drug's peripheral pharmacokinetic (PK) profile. The patients may find themselves during the day in either ON state, when the patients are capable of normal movement, or in OFF state, wherein the patients suffer from impaired movement. As the disease progresses, the patients begin to fluctuate between the two states. These fluctuations are often accompanied by troublesome diskinesias in ON state and deep OFF state, wherein movement is severely impaired. Hence, improving consistency of LD's plasma levels is essential for improving its anti-Parkinson effects.

In addition, in current treatment, physicians fractionate LD doses in an attempt to reduce the pulsed action of fewer, larger doses, and to stabilize the LD's pharmacokinetic (PK) profile. Hence, a significant pill burden is another major concern, associated with LD treatment. Advanced PD patients often take up to 8-10 LD doses a day, trying to stabilize their motor conditions.

For these reasons, numerous efforts have been made by many pharmaceutical companies over the years to develop an effective long-acting LD. Available controlled-release preparations of LD currently on the market do not maintain sufficiently high LD plasma levels. The reason is that in addition to its very short half-life (90 min), LD is absorbed mainly in the upper part of the GI tract. Once a typical controlled-release formulation has passed the drug's narrow absorption window in the upper part of the GI, the drug is no longer absorbed in the distal intestine, regardless of the manner it is released from the dosage form.

Another concern with current LD treatment is that rapid elimination of LD and lack of means to sustain relevant LD levels for prolonged time intervals lead to the absence of sufficiently high LD plasma levels in patients in the morning, causing movement arrest and necessitating ultra-rapid LD dosage forms, generally unavailable on the market, or parenteral preparations which are cumbersome for self administration in deep OFF state.

The symptoms of PD in patients are frequently expressed as Unified Parkinson's Disease Rating Scale (UPDRS) score. Most frequently, so-called "part 3" is used in evaluation by a clinician of motor abilities/impairment of PD patients. The UPDRS was recently reviewed and updated, and is regarded as a standard mean to evaluate PD patients (see Movement Disorders, Vol. 22, No. 1, 2007, pp. 41-47; *Movement Disorder Society-Sponsored Revision of the Unified Parkinson's Disease Rating Scale (MDS-UPDRS): Process, Format, and Clinimetric Testing Plan*, by Dr. Christopher G. Goetz et al, doi: 10.1002/mds.21198).

It is postulated that gastric retention could significantly prolong the LD's absorption phase, by retaining the drug in proximity to its absorption site and releasing the drug in a continuous manner, towards that absorption site. Some examples of gastroretentive LD delivery systems are disclosed in WO2009/144558 (Intec Pharma), which is herein incorporated by reference in its entirety. These gastroretentive formulations are also frequently referred to as "Accordion Pill", or AP. Alternatively, some gastric retentive pharmaceutical compositions for treatment and prevention of CNS disorders are disclosed in WO2010/019915 (Depomed).

Hence, the challenge is to develop an oral, effective long-acting LD regimen that provides significantly more continuous and stable relevant LD plasma levels over 24 hours, with reduced Total OFF Time and significantly reduced doses per day, preferably a twice-daily dosing.

SUMMARY OF THE INVENTION

The present invention is directed to overcoming the problems of the prior art described above.

Thus, in one embodiment, the invention provides for the use of an accordion pill comprising levodopa for the treatment of symptoms of Parkinson's disease in a subject in need thereof over a 24 hour period. The accordion pill comprising levodopa is administered to the subject in a twice daily administration regimen, as a first dose and as a second dose, with an interval of about 8 to about 10 hours between the first dose and the second dose, and with an interval of about 14 to about 16 hours between the second dose and the first dose of the following day. In a preferred aspect of the invention, the twice daily administration regimen provides a stable blood plasma level of levodopa in the subject after multiple administrations. In an even more preferred aspect of the invention, the stable blood plasma levels of levodopa are effective in treating the symptoms of Parkinson's disease over a 24 hour period following the administration of the first dose.

In one embodiment, the accordion pill comprises about 250 mg levodopa, and the twice daily administration regimen provides after multiple administrations average blood plasma levels of levodopa of 200-1,000 ng/ml in the subject over a 24 hour period following administration of the first dose.

In a different embodiment, the accordion pill comprises about 375 mg levodopa, and wherein the twice daily administration regimen provides after multiple administrations average blood plasma levels of levodopa of 500-1,500 ng/ml in the subject over a 24 hour period following administration of the first dose.

In yet another embodiment, the accordion pill comprises about 500 mg levodopa, and the twice daily administration regimen provides after multiple administrations average blood plasma levels of levodopa of 700-2,000 ng/ml in the subject over a 24 hour period following administration of the first dose.

In some embodiments, the accordion pill of the twice daily administration regimen provides absorption of levodopa into the blood plasma of the subject for about 6 to about 14 hours following administration of the accordion pill.

In one aspect of the invention, the twice daily administration regimen further comprises administering to the subject one or more dosage forms comprising immediate-release or controlled-release levodopa.

In a preferred embodiment, the stable blood plasma level of levodopa in the subject provides an absolute peak-to-trough ratio of levodopa blood plasma concentrations below 7.

In another preferred embodiment, the twice daily administration regimen reduces peak-to trough fluctuations in the blood plasma levels of levodopa in the subject by at least 50% in comparison to immediate-release formulations comprising daily equal-doses administered four times a day.

In one aspect of the invention, the twice daily administration regimen shortens or eliminates total OFF time during waking hours in the subject. In a different aspect of the invention, the twice daily administration regimen allows faster onset of the ON period in the subject.

In a preferred embodiment, the twice daily administration regimen alleviates or eliminates nightly sleep disturbances and daytime sleepiness or drowsiness in the subject.

In a different aspect of the invention, the twice daily administration regimen further comprises administering to the subject one or more add-on dosage forms comprising immediate-release or controlled-release levodopa.

In an additional embodiment, the invention provides for the use of an accordion pill comprising levodopa for the treatment of symptoms of Parkinson's disease in a subject in need thereof over a 24 hour period. The accordion pill comprising levodopa is administered to the subject in a twice daily administration regimen, with an interval of about 8 to about 10 hours between the first dose and the second dose, and with an interval of about 14 to about 16 hours between the second dose and the first dose of the following day.

Preferably, the twice daily administration regimen provides a stable blood plasma level of levodopa in the subject after multiple administrations. In a preferred aspect of the invention, the stable blood plasma level of levodopa in the subject is effective in treating the symptoms of Parkinson's disease over a 24 hour period following the administration of the first dose.

In an even more preferred aspect of the invention, the twice daily administration regimen of the invention produces significantly high morning levels of levodopa in the blood plasma of the subject. Preferably, the significantly high morning levels of levodopa in the blood plasma of the subject allow faster onset of the ON period or shorten the OFF period after the first levodopa administration of the day.

In one preferred aspect of the invention, the twice daily administration regimen alleviates or eliminates nightly sleep disturbances and daytime sleepiness or drowsiness in the subject.

In one embodiment, the accordion pill comprises about 250 mg levodopa, and the twice daily administration regimen provides after multiple administrations average blood plasma levels of levodopa of 200-1.000 ng/ml in the subject over a 24 hour period following administration of the first dose.

In a different embodiment, the accordion pill comprises about 375 mg levodopa, and wherein the twice daily administration regimen provides after multiple administrations average blood plasma levels of levodopa of 500-1,500 ng/ml in the subject over a 24 hour period following administration of the first dose.

In yet another embodiment, the accordion pill comprises about 500 mg levodopa, and the twice daily administration regimen provides after multiple administrations average blood plasma levels of levodopa of 700-2,000 ng/ml in the subject over a 24 hour period following administration of the first dose.

In one aspect of the invention, the accordion pill may further comprise about 50 mg to about 75 mg of carbidopa. In a preferred aspect of the invention, the twice daily administration regimen provides carbidopa blood plasma levels sufficient to adequately prevent peripheral levodopa side effects in the subject for a 24 hour period.

In a preferred aspect of the invention, the stable blood plasma level of levodopa in the subject after multiple administrations provides values of area-under-the-curve over 24 hours and a relative bioavailability that is not less than 85% relative to the values obtained from immediate-release formulations comprising daily equal doses administered four times a day. Alternatively, the stable blood plasma levels of levodopa in the subject after a single administration provides values of area-under-the-curve extrapolated to infinity and a relative bioavailability that is not less than 85% relative to the values obtained from immediate-release formulations comprising equal doses of levodopa.

In preferred embodiments, the twice daily administration regimen of the invention after multiple administrations provides a reduction of total OFF time during waking hours from about 3 hours to about 1 hour. Alternatively, the twice daily administration regimen of the invention after multiple administrations provides a reduction in total OFF time during waking hours of not less than 50% in comparison to the total OFF time associated with the administration of optimized prior treatment of the subject with levodopa.

In yet a different aspect, the invention provides for the use of an accordion pill comprising levodopa for the treatment of symptoms responsive to levodopa in a subjects in need thereof over a nocturnal period. The accordion pill comprising levodopa is preferably administered at bed time. In a preferred aspect of the invention, bed time administration improves sleep quality during the night following administration. In an even more preferred aspect of the invention, bed time administration alleviates or eliminates the symptoms of morning akinesia or morning dystonia.

The foregoing general description and the detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

Definitions

Figure 1:
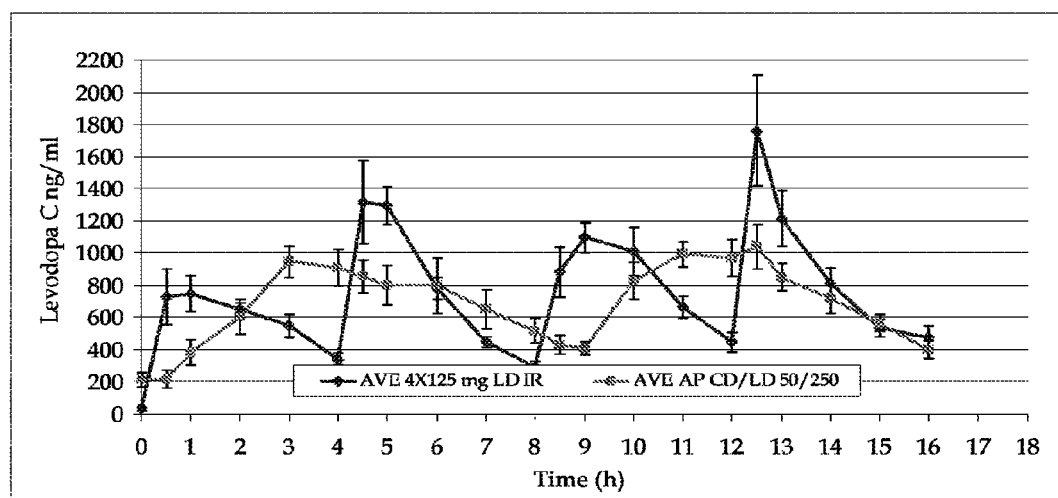
FIG. 1 presents the results of a pharmacokinetic equidose study in early PD patients with AP CD/LD 50/250 mg, administered b.i.d vs IR q.i.d.

"Gastroretentive dosage form", or "Accordion Pill", or "AP", as used interchangeably herein refers to dosage forms with delayed gastric emptying as compared to food or to regular oral drug formulations (or retention in the stomach beyond the retention of food). In particular, the term refers to a multilayered gastroretentive dosage form, folded into a capsule in undulated form, which unfolds upon contact with the gastric fluids.

The term "degradable" as used herein is intended as capable of being chemically and/or physically reduced, dissolved or broken down in the body of a patient and within a relevant time period.

A "patient" or "subject" as referenced herein is a human or non-human mammal suffering from symptoms of Parkinson's disease or of a related disorder.

"Treating" or "treatment", are used herein to refer to obtaining a desired pharmacological and physiological effect. The effect may be prophylactic in terms of preventing or partially preventing a disease, symptom or pathological condition and/or may be therapeutic in terms of a partial or complete cure of a disease, condition, symptom or adverse effect attributed to a pathological condition. Thus, "treatment" covers any treatment of a disease in a mammal, particularly a human, and includes: (a) preventing a pathological condition from occurring in an individual which may be predisposed to develop a pathological condition but has not yet been diagnosed as having it, i.e., causing the clinical symptoms of a pathological condition not to develop in a subject that may be predisposed to develop the condition but does not yet experience or display symptoms of the condition; (b) inhibiting, i.e., arresting or reducing the development of the pathological condition or its clinical symptoms; or (c) relieving symptoms associating with the pathological condition. In particular, the term refers to alleviating symptoms of Parkinson's disease and of related movement disorders, clinically responsive to levodopa.

"About" as used herein generally refers to approximate values. When referred to a dose of LD in milligrams, "about" should be construed as including the range of a value ±50 mg. When referred to time intervals of dose administration, "about" should be construed as including the range of a value ±1.0 hour. When referred to pharmacodynamic values of total ON or total OFF time, during waking hours or over 24 hours, the term should be construed as including the range of a value ±0.15 hour. When referred to blood plasma levels of LD and other values, the term should be construed as including the range of a value ±15%

The term "equidose", or "equal-dose", as used interchangeably herein, refers to as containing the same total dose of an active material, administered over the dosing regimen, particularly, over 24 hours periods.

"Add-on dose", or "rescue dose", as used interchangeably herein, refer to a medicinal product comprising levodopa. An add-on dose provides additional levodopa to the regimen of the present invention. Sometimes add-on doses are taken by the patients to expedite the arrival to ON state. The term should be construed as including an immediate-release product comprising levodopa, or a controlled-release product, comprising levodopa.

"Effective LD blood plasma levels", as used herein, refer to LD levels that provide the desired pharmacodynamic effect in a subject in need of treatment with minimal side effects. For early non-fluctuating PD patients the effective LD blood plasma levels are usually not less than about 200 ng/ml at any point of time for 24 hours after administration of a first dose of the regimen. The effective LD blood plasma levels usually do not exceed about 1000 ng/ml. In more advanced non-fluctuating PD patients, the effective LD blood plasma levels are usually not less than about 300 ng/ml, and preferably above about 500 ng/ml, and do not exceed about 1500 ng/ml. In fluctuating PD patients, the effective LD blood plasma levels are usually greater than about 500 ng/ml, and preferably greater than about 700 ng/ml, and do not exceed about 2000 ng/ml over a 24-hours period after administration of a first dose of the regimen.

"Significantly High Morning LD levels", as used herein, are the LD levels achieved by PD patients as a result of multiple administrations according to the regimen of the invention about 0.5 hour or just prior to administration of the first dose of the consecutive treatment day. In early non-fluctuating patients these levels are usually above about 200 ng/ml. In more advanced non-fluctuating PD patients, the significantly high morning LD levels are not less than about 300 ng/ml and preferably above about 500 ng/ml. In fluctuating PD patients, the significantly high morning LD levels are above about 500 ng/ml, and preferably above about 700 ng/ml. The term is used as opposed to "significantly low morning LD levels", which should be construed as confined to the values significantly below the above described.

"Relevant therapeutic LD levels throughout the night" and "Significant night levels of LD", as used interchangeably herein, are effective nocturnal LD blood plasma levels that lead to significantly high morning LD levels.

"LD Elimination Half Life", as used herein, is a pharmacokinetic parameter as known in the art, and represents the time required for levodopa blood plasma concentration to decrease to half of its initial value in absence of input of levodopa to the bloodstream.

"Short Absorption phase", as used herein, is an absorption phase having a duration of less than 14 hours, and preferably less than 6 hours.

"Long arrival to ON state" and "Long duration of OFF time upon administration of a subsequent dose", as used interchangeably herein, relate to the buildup of LD blood plasma levels required for conventional formulations for arrival usually from significantly low morning LD levels to effective LD blood plasma levels, as opposed to the "Quick arrival to ON state" and "Faster onset of the ON period", as used interchangeably herein, which refer usually to the arrival from significantly high morning LD levels to effective LD blood plasma levels, said arrival does not require significant buildup of LD blood plasma levels. More specifically, the terms refer to the time intervals required for a patient to reach ON state following the first administration of LD of the day.

"Morning OFF time", as used herein, refers to the time interval between the administration to a PD subject LD and the subject's arrival to ON state following the administration. Morning OFF time is usually associated with significantly low morning LD blood plasma levels.

"Repetitive dosing", or "multiple administrations", as used interchangeably herein, refers to repetitive administration of LD according to a specified dosing regimen, for period over more than one day.

Induce rapidly ON state—as used herein, refers to a process of rapid arrival to ON state, usually as a consequence of administration of an add-on dose of levodopa, an immediate-release dose of levodopa, or prematurely taking a consecutive dose of a treatment. In the description herein, the term usually refers to current treatment regimens of levodopa.

"Peak-to-trough ratio", as used herein, refers to the ratio between the peak concentration of the regimen (Cmax) and the trough concentration of the regimen (Cmin) over 24 hours period.

"Absolute fluctuation", as used herein, refers to the mathematical difference between the peak concentration of the regimen (Cmax) and the trough concentration of the regimen (Cmin) over 24 hours period.

"Total OFF time", as used herein, refers to the duration of total of all OFF episodes over a specified time interval, either during waking hours, or over 24 hours.

"Total ON time", as used herein, refers to the overall duration of all ON episodes over a specified time interval, either during waking hours, or over 24 hours.

"Significant Reduction", as used herein, refers to a statistically significant reduction as measured by ANOVA test ($\alpha=0.05$) (P value below 0.05).

"Better sleep quality", as used herein, refers to improved sleep quality, defined by fewer mid-night awakenings, increased total sleep time and extended depth of sleep.

The Accordion Pill (AP)

The Accordion Pill (AP) is a dosage form designed to significantly increase efficacy and/or to reduce adverse drug reactions (ADRs) and/or frequent daily dosing of drugs that are characterized by poor absorption in the colon or which absorption is confined to yet narrower sites. The AP is retained in the stomach and releases the drug in a predetermined release profile, enabling a prolonged exposure to the absorption area in the upper part of the small intestine, hence—to significantly prolong the actual absorption phase of the drug.

The Accordion Pill is composed of degradable pharmaceutically acceptable polymeric films. The films are layered sandwich style and are folded in an undulated structure, like an accordion, into a standard capsule. After oral administration, the capsule dissolves and the dosage form unfolds and is retained in the stomach. While in the stomach, the Accordion Pill releases the active ingredients in a predetermined release profile (controlled release or combination of immediate and controlled release). Once the AP is expelled from the stomach and reaches the intestines, it degrades m the higher pH and within a few hours it totally dissolves.

Certain delivery systems of AP-CD/LD are disclosed in WO2009/144558, which is herein incorporated by reference in its entirety.

In preferred embodiments, the AP-CD/LD comprises an internal layer, one or more outer membranes, preferably two, sandwiching said internal layer, all said layers being ultrasonically welded together.

The internal layer comprises levodopa and a polymer, substantially uniformly distributed throughout the internal layer. The polymer may be selected from the group consisting of a degradable hydrophilic polymer which is not instantly soluble in gastric fluid, a degradable enteric polymer which is substantially insoluble at pH less than 5.5, a hydrophobic polymer, or mixtures thereof. Said internal layer may further comprise acceptable pharmaceutical additives, such as plasticizers, humectants, fillers and others. Examples of such additives are provided in various sources in the art, for example in the "Handbook of pharmaceutical excipients", edited by Rowe, Ray C; Sheskey, Paul J; Quinn, Marian, printed by Pharmaceutical Press. Examples of degradable hydrophilic polymers which are not instantly soluble in gastric fluid suitable for the invention include but not limited to hydroxypropyl cellulose, hydroxypropylmethyl cellulose, polyvinyl pyrrolidone, copovidone, polyethylene oxide, poloxamers and methylcellulose. Examples of the enteric polymers include but not limited to polymethacrylate copolymers, cellulose acetate phthalate, hypromelose acetate succinate or hypromellose phthalate. Examples of hydrophobic polymers include but not limited to ethyl cellulose, cellulose acetate, cellulose butyrate and polyvinyl acetate. In further preferred embodiments, the internal layer comprises levodopa, an enteric polymer, a degradable hydrophilic polymer which is not instantly soluble in gastric fluid and a plasticizer. In further preferred embodiments, the enteric polymer is polymethacrylate copolymer-methacrylic acid copolymer type A or methacrylic acid copolymer type B, as defined in the United States Pharmacopea 34/National Formulary 29 (USP/NF). These materials are also known under newer specifications of the USP/NF as "methacrylic acid and methyl methacrylate copolymer (1:1)", and "methacrylic acid and methyl methacrylate copolymer (1:2)", respectively. In another preferred embodiment, the plasticizer is a mixture of polyethylene glycol and a poloxamer. In yet further preferred embodiments, the internal layer provides substantial mechanical strength.

Each of the outer membranes of the AP-CD/LD comprises at least one polymeric combination of a hydrophilic polymer and a polymer, insoluble in gastric media, and at least one plasticizer. Examples of hydrophilic polymers include but not limited to gelatin, hydroxypropylcellulose, hydroxypopyl methycellulose, pectin, polyethylene oxide, starch, and zein. In preferred embodiments, the hydrophilic polymer is gelatin. The enteric polymers suitable for the outer membranes include but not limited to hypromellose phthalate, hypromellose acetate succinate and polymethacrylate co-polymers. In preferred embodiments, the enteric polymer is polymethacrylate copolymer-methacrylic acid copolymer type A or methacrylic acid copolymer type C, as defined in the USP/NF, or, under newer definitions, "methacrylic acid and methyl methacrylate copolymer (1:1)" and "methacrylic acid and ethyl acrylate copolymer (1:1)". Plasticizers suitable for the outer membrane include but not limited to glycols, including various MW polyethylene glycols, glycerin, poloxamers, triethyl citrate, or a mixture of any of the above. In a preferred embodiment, the plasticizer is propylene glycol. In another preferred embodiment, the plasticizer is a mixture of polyethylene glycol and poloxamer.

In various embodiments, the outer membranes swell in the presence of gastric fluid.

In preferred embodiments, the internal layer and two outer layers are joined together by ultrasonic welding. The combination of swelling outer membrane layers with a non-swelling internal layer having planar accordion geometry causes the internal layer to undergo an unfolding process once the formulation reaches the stomach, thus extending gastric residence time and preventing the drug-containing dosage form from being evacuated until complete release. In some embodiments the internal layer has a swelling rate less than the swelling rate of the membrane.

In some embodiments, the AP-CD/LD comprises an internal layer and at least two outer membranes as described above, and may further comprise additionally one or more immediate release layers covering the outer membranes and comprising the active agent and a composition that provides for the immediate release of the active agent. In some embodiments, the additional layer comprises levodopa. In other embodiments, said additional layer comprises carbidopa. In preferred embodiments, two additional layers are provided covering both outer membranes, wherein a first additional layer comprises levodopa, and a second additional layer comprises carbidopa. Said composition may comprise soluble polymers, enteric polymers, plasticizers, disintegrants, surface-active agents and other pharmaceutical excipients, as described above.

In several embodiments, the soluble polymers of said composition for the use in said additional layers include but not limited to soluble cellulose derivatives, i.e. methyl cellulose, hydroxypropyl cellulose, hydroxyethyl cellulose, hypromelose, various grades of povidone, including copovidone, polyvinyl alcohol and its derivatives, i.e. Kollicoat IR, soluble gums and others. The composition for the use in said additional layers may further include surface-active agents, plasticizers and humectants, such as PEGs, different grades of polysorbates and sodium lauryl sulfate. In several embodiments, the enteric polymers of said composition for the use in said additional layers include but not limited to polymethacrylate copolymers, hypromellose phthalate, hypromellose acetate succinate, cellulose acetate phthalate, or a mixture thereof. In preferred embodiments, the polymer is methacrylic acid copolymer type C, also known as "methacrylic acid and ethyl acrylate copolymer (1:1)", as described in the USP/NF. In several preferred embodiments, said composition further comprises a disintegrant. Disintegrants imbibe water upon contact and swell rapidly to provide separation of the adjacent parts. The disintegrant of said composition for the use in said additional layers is crospovidone, croscarmellose, sodium starch glycolate, or mixtures of the above. In preferred embodiments, the disintegrant is sodium starch glycolate.

In further embodiments, the AP-CD/LD may further comprise an optional additional layer covering each outer membrane or each additional layer and comprising a powder or a film. The purpose of the layer is to avoid adhesion of the folds of the undulated form of AP-CD/LD upon capsulation, and the adhesion of the folds to the capsule. In some instances it may be found that the outer layers stick together in the capsule and do not unfold properly upon dissolving of the capsule. In preferred embodiments, said optional layer comprises at least one powder, and optionally at least one polymer. In other embodiments the preferred polymers are rapidly-dissolving film formers, which can be selected from but not limited to soluble cellulose derivatives, i.e. methyl cellulose, hydroxypropyl cellulose, hydroxyethyl cellulose, hypromelose; various grades of povidone; polyvinyl alcohol and its derivatives, i.e. Kollicoat IR; soluble gums and others. The films may further comprise surface-active agents, plasticizers and humectants. The powders that may be used in said optional layer include but not limited to microcrystalline cellulose, talc, silica, colloidal silicon dioxide, a clay or a mixture of any of the above. In preferred embodiments, said optional layer comprises microcrystalline cellulose.

In all embodiments of the present invention, the AP-CD/LD is folded into undulated form and compacted into a standard pharmaceutical capsule.

The Dosing Regimen

The present invention provides a twice daily administration regimen of AP-CD/LD formulations in doses such as, for example, a 50/250 mg dosage form, targeted for early stage PD patients; 50/500 or 50/530 mg dosage forms targeted for advances stage PD patients; and 50/375 mg or 50/405 mg dosage forms for treatment of both populations. In preferred embodiments, the twice daily administration regimen of the AP-CD/LD formulations of the invention provide effective blood plasma level of levodopa for time intervals of about 24 hours, due to the absorption phase, provided by AP-CD/LD, which is between about 6 to about 14 hours. In an even more preferred embodiment, of the absorption phase, provided by AP-CD/LD formulations of the invention are longer than 14 hours.

Figure 4:
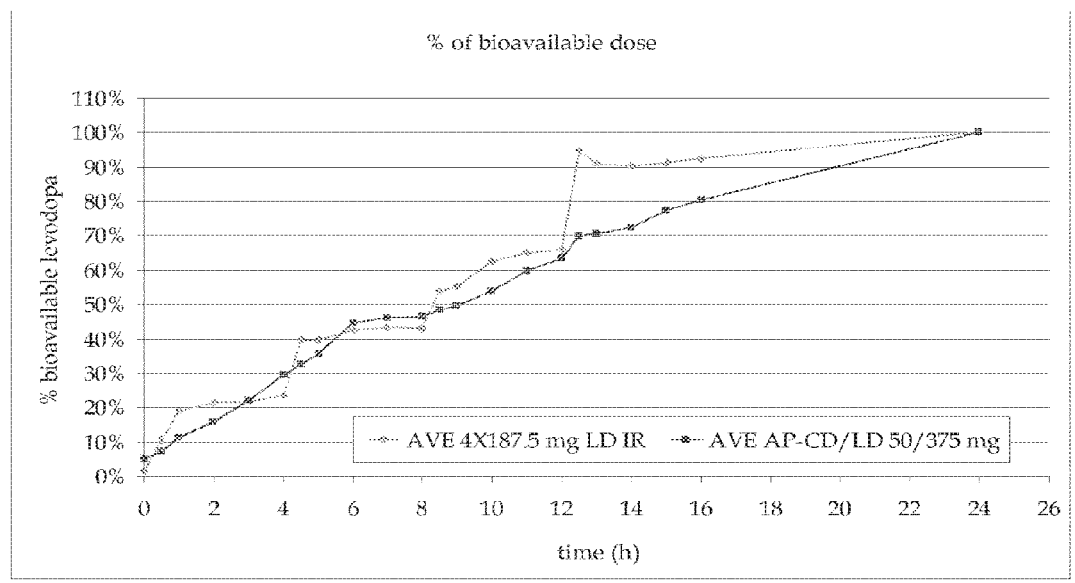
FIG. 4 presents the levodopa absorption profile as percentage of total bioavailable dose, as calculated from the data of the example 2.

The length of the absorption phase is exemplified by the data presented in the examples provided herein. Absorption data may be obtained from the concentration-vs-time curve by methods known in the art. These include modeling and de-convolution of functions, which describe the absorption. One of the approaches is known as Wagner-Nelson approach. The analysis of the data presented in Example 2 using Wagner-Nelson approach yields an absorption curve, which is presented in FIG. 4. The doses were administered at time 0, and after 8 hours. FIG. 4 shows that the major absorption phase throughout the dosing regimen, for 24 hours, indicating individual absorption phases of over 6 hours, and over 14 hours, exemplifying some of the preferred embodiments. Alternatively, the absorption phase may have duration of 6.5 hours, or 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, or 16.0 hours.

In the use of the oral dosage forms of levodopa disclosed in the invention, said dosage forms are administered twice a day, in a regimen generally known as b.i.d. regimen. Conventionally, the b.i.d. regimen is considered as administration every 12 hours. In some embodiments of the present invention, the two doses are administered twice daily, every 12 hours. However, in preferred embodiments of present invention, the two doses of levodopa from the oral dosage form of the invention are administered as a first administration of a day and a second administration of the same day, with an interval of about 8 to about 10 hours between the first dose administration and the administration of a second dose of levodopa, and with an interval of about 14 to about 16 hours between the second dose of the first day and the first dose of the following consecutive day. Whereas generally the preference is that the described interval between the first administration and the second administration is 8 to 10 hours, the second dose can be administered about 6.0 hours after administration of the first dose, or 6.5 hours, or 7.0 hours, or 7.5, hours, or 8.0 hours, or 8.5 hours, or 9.0 hours, or 9.5 hours, or 10.0 hours, or 10.5 hours, or 11 hours after administration of the first dose. The regimen of administration of the two dosage forms according to the invention provides effective LD blood plasma levels in the subject for 24 hour consecutive periods. Furthermore, repetitive administration of LD according to the specified dosing regimen ("repetitive dosing") provides stable effective LD blood plasma levels in the subject for extended consecutive periods of time and decreases or prevents fluctuations in the blood plasma level of LD in the subject. In all aspects and embodiments of the present invention, the repetitive dosing, or multiple administrations, are referred to a period having duration of more than one day, for example, 2 days, 3 days, 4, 5, or 6 days, 1 week, 2 weeks or 3 weeks, 1 month, 1.5 months, 2 months, or 3 months. In principle, said twice-daily treatment regimen of the present invention may be continued in the same or varied dosing and intervals for as long as benefit to a patient is sustained.

Sleep quality is another major issue in PD. Entering into OFF state during the sleep leads to awakening of the patients, and poses a problem to fall asleep again. As shown in the examples of the present application, the regimen of administration of the two dosage forms according to the invention results in morning LD levels in the blood plasma of a patient that are significantly higher than the morning blood plasma LD levels provided by known current treatment methods. The significantly high morning blood plasma LD levels that the invention provides indicate that the administration regimen of the invention maintains therapeutic LD levels in the blood plasma of the subject being treated throughout the night, and leads to clinically relevant, stable concentrations of LD in the blood plasma of the subject. In turn, the retention of therapeutic LD levels throughout the night improves quality of sleep and reduces day time sleepiness in the subject being treated.

Normally, LD does not reach continuously effective LD blood plasma level when administered as immediate or controlled-release dosage forms, due to LD short elimination half-life and short absorption phase provided by these dosage forms; the parameters are not sufficiently increased by conventional controlled-release dosage forms. As a result, conventional regimens do not afford significant blood plasma night levels of LD, thereby reducing quality of sleep, and as a result causing day sleepiness and drowsiness, as described above. In addition, the lack of therapeutic LD blood plasma levels throughout the night leads to low morning LD blood plasma levels, significantly prolongs the duration of OFF time upon administration of a subsequent dose the next day, and results in a delayed arrival to the ON state, because the process requires a large LD blood plasma level buildup to reach the ON state. Frequently, to overcome the problem, the patients use high doses of IR levodopa, thus increasing fluctuations of blood plasma levels of LD.

The twice daily administration regimen of the invention, wherein the two LD doses are administered with an interval of about 8 to about 10 hours between the first dose of a day and the second dose of the same day, and with an interval of about 14 to about 16 hours between the second LD dose of the first day and the first LD dose of the following consecutive day, affords effective night levels and thus reduces, alleviates or potentially eliminates nightly sleep disturbances and daytime sleepiness or drowsiness, which are major issues in subjects suffering from Parkinson's disease. Furthermore, the twice daily administration regimen of the invention produces significantly high morning levels of LD, shortens or eliminates morning OFF time, and, because of the significantly high morning levels of LD, results in a quicker arrival to the ON state upon administration of the first dose in the consecutive morning, since the process does not require LD blood plasma level buildup to reach the ON state. Upon a particular need, regular or reduced doses of LD can be used to arrive quickly to ON state.

LD is released from the oral dosage forms administered according to the regimen of the invention providing relatively stable LD blood plasma levels in the subjects being treated for extended periods of time. Surprisingly, the LD blood plasma levels are sustained for 24 hours in the subject after repetitive dosing according to the regimen. In one embodiment, the dose of LD in the oral dosage form is about 250 mg, and under the b.i.d. regimen of 8-10 h, as described above, the blood plasma in the subject being treated reaches a stable LD level of 200-1,000 ng/ml. The blood plasma levels of levodopa would be therefore generally more than about 200 ng/ml, or 180, 200, 220, 240, 250, 260, 280 or 300 ng/ml, and generally less than 1000 ng/ml, or 980, 950, 925, 900, or 875 ng/ml. In another embodiment, the dose of LD in the oral dosage form is about 375 to about 405 mg, and the blood plasma of the subject being treated reaches a stable LD level of about 500-1,500 ng/ml. The blood plasma levels of levodopa would be therefore generally more than about 500 ng/ml, or 450, 475, 500, 525, 550, 575, 600, 650 or 700 ng/ml, and generally less than 1500 ng/ml, or 1475, 1450, 1425, 1400, 1350, or 1300 ng/ml. In yet another embodiment, the dose of LD in the oral dosage form is from about 500 to about 530 mg, and the blood plasma of the subject being treated reaches a stable LD level of about 700-2,000 ng/ml. The blood plasma levels of levodopa would be therefore generally more than about 700 ng/ml, or 625, 650, 675, 700, 725, 750, 775, 800, 825 or 850 ng/ml, and generally less than 2000 ng/ml, or 1950, 1925, 1900, 1875, 1850, 1825 or 1800 ng/ml.

In one aspect of the invention, the two oral dosage forms administered according to the regimen of the invention contain the same dose of LD. In alternative embodiments, the doses are different to accommodate the needs of the patient in either the first part of the day or the second part of the day. One patient may require higher levels in the afternoon, whereas another may require higher levels in the first part of the day. The doses can be varied by the prescriber to obtain optimal efficacy over 24 hours, according to individual needs of the patients. This gives rise to asymmetrical regimens, whereby the first dose is not necessarily equal to the second. In alternating multiple embodiments, there are many such combinations possible, exemplified but not limited to 250 mg in the morning and 250 mg in the afternoon, 250 mg in the morning and 375 mg in the afternoon, 375 mg in the morning and 500 mg in the afternoon, 250 mg in the morning and 500 mg in the afternoon, or 500 mg in the morning and 375 mg in the afternoon. Any such or similar combination represents the basal treatment regimen and provide treatment of Parkinson's disease symptoms over 24 hours, when administered to a patient in need thereof in an interval of about 8 to 10 hours, after repetitive dosing, thereby providing stable efficacious blood plasma levels of LD.

The treatment provided according to the regimen of the invention may be optionally enhanced by administration of "add-on" doses. These comprise dosage forms comprising LD for either immediate release (IR), or controlled release (CR), or a combination thereof. The need for these add-on doses arises from inevitable intra-subject variability, meaning that the same subject may not react the same way to the same dosage form administered on a different day. This intra-subject variability in day-to-day response to LD is well-known in PD treatment. The add-on doses are vastly used in current treatment schedules to induce rapidly ON state and to end OFF state. The current regimens overburden the patients with the doses of LD. The disclosed regimen overcomes this problem, as it cumulatively requires substantially fewer number of LD doses per day, than needed with current treatments. Therefore, in some embodiments, said twice-daily regimen further comprises administration of one or more add-on LD doses. In some embodiments, said add-on doses are immediate-release doses. In alternative embodiments, said add-on doses are controlled release doses. In other embodiments, said doses comprise mixed immediate-release and controlled-release doses. In several embodiments, said doses are administered on the same time every treatment day. Alternatively, said add-on doses may be administered as needed on varying time during the treatment day.

Conventional dosing regimens frequently result in high fluctuations. The peak-to-trough ratio is usually used to evaluate the fluctuations of blood plasma levels of a drug. Alternatively, when comparing dosing regimens, sometimes absolute fluctuation values are used to express the degree of change that certain dosage form produces. Fluctuations of levodopa blood plasma levels in subjects treated with the conventional formulations are very high, due to rapid elimination and limited absorption window of the conventional dosage forms.

The peak-to-trough ratio is calculated as maximal concentration achieved during the 24-hours period, over minimal concentration over the same period. Said ratio is 1 for continuous delivery dosage forms, such as intravenous infusion. Current treatment of immediate-release presents ratio of over 40. In several embodiments of the present invention, said ratio is below about 10, preferably below about 9.5, 9.0, 8.5, 8.0, 7.5, or 7. Alternatively, the fluctuations may be expressed by comparison to current treatment, and the fluctuations produced by the twice-daily regimen of the invention are reduced at least by about 50%, or by 44%, 46%, 48%, 50%, 52%, 54%, 56%, 58%, 62% or 64% in comparison to conventional daily equal-dose IR treatment four times a day. In preferred embodiments, said fluctuations are reduced by about 60%.

The reduction in LD blood plasma fluctuations provided by the regimen of the invention decreases adverse effects associated with LD treatment. Most significantly, the total OFF time during waking hours decreases, and total ON time increases. The side effects are usually associated with more progressive stage of the disease. Administration of an oral dosage form of LD comprising about 375 mg or about 500 mg of LD according to the regimen of the invention with an interval of 8 to about 10 hours between the first and the second dose to a patient in need thereof produces a significant reduction of total OFF time during waking hours. Alternatively, two dosage forms, with an LD amount of 375 mg and 500 mg, respectively, may be administered to a subject in need thereof according to the regimen of the invention for the treatment of symptoms of Parkinson's disease. Such administration leads to a significant reduction of total OFF time during the subject's waking hours. Similarly, the reduction of total OFF time in patients in need thereof can be enhanced by incorporating into said regimen at least one add-on. Similarly to the described above, said add-on doses may comprise an IR levodopa dose, a CR levodopa dose, or a mixture of the IR and CR levodopa dose. The doses may be taken preferably as fixed-time dose, or alternatively, on "as needed" basis, as rescue dose for the interruption or alleviation of the OFF state, thereby enhancing reduction of total OFF time during waking hours. Alternatively, a method of treatment is provided, for reduction or alleviation of Parkinson's disease symptoms in patients in need thereof, said method comprising administration any of two oral dosage forms, comprising about 375 mg of LD, or about 500 mg of LD each, according to the regimen of the invention, which method further comprises administration of one or more add-on doses of IR or CR levodopa.

The effectiveness of an anti-parkinson treatment is estimated as reduction in total OFF time, or as reduction of total OFF time during waking hours, sometimes used interchangeably. The total OFF time is an important parameter and varies within the population of PD patients, according to the severity of the disease. Early patients have very short periods of OFF during the waking hours, or do not suffer at all from the OFF phenomenon. As the disease advances, the patients may reach total OFF time of 0.5 hour to over 6.5 hours, and sometimes even to over 8.0 hours. In yet more advanced stage, the patients reach these "total OFF" values even being treated adequately by best available regimens. The treatment provided according to the regimen of the invention significantly reduces total OFF time. In some embodiments, the total OFF time during waking hours is reduced by at least about 45%, but can be decreased by 44%, 45%, 46%, 48%, 52%, 54%, 56%, 58%, 60%, 62% or by 64%, versus either baseline values or versus the optimized LD treatment of a subject. In other preferred embodiment, the treatment provided according to the regimen of invention reduces total OFF time by at least 1.2 hours, but can be decreased by 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or by 5.0 hours. In further preferred embodiments, the regimen of present invention provides a reduction in total OFF time during waking hours from 2.9 hours to 1.2 hours, versus optimized levodopa treatment in the subject. In yet further preferred embodiments, the reduction is obtained by administering to the patient in need the AP-CD/LD 375 mg twice daily, according to the regimen of the invention, without or practically without add-on doses (dosing frequency 2.2±0.2 per 24 hours).

Conventional regimens of LD treatment do not provide the subject being treated with significantly high morning levels of LD, as described above. Moreover, PD patients frequently suffer from night OFF state, whereby the patients are awakened by their incapacity to move during their sleep. This sometimes results in the need to take nocturnal LD doses. These subjects suffer from drowsiness and daytime sleepiness, as a result of night awakening. The overall quality of life of these patients may deteriorate. Taking higher LD doses at bedtime does not solve the problem, as LD is rapidly removed from the bloodstream and its absorption is limited to a maximum of two hours of the narrow absorption window. Moreover, taking overdoses of LD can result in troublesome diskinesias, expressed by involuntary movements, which further impede falling asleep and offer no solution. A large number of subjects affected by PD and facing fluctuations in their blood plasma LD level are thus compelled to use sleep-inducing medicines, which further burden the patient with yet a higher pill-load and increases the risk of drug-to-drug interactions.

The treatment regimen of the present invention resolves these issues by providing high blood plasma LD levels in the morning over 24 hour periods in subjects in need of treatment of Parkinson's disease symptoms. The twice daily administration regimen of the invention, wherein the two LD doses are administered with an interval of about 8 to about 10 hours between the first dose of a day and the second dose of the same day, and with an interval of about 14 to about 16 hours between the second, pre-midnight LD dose of the first day and the first LD dose of the following consecutive day, provides the subjects being treated with stable, effective LD blood plasma concentrations for consecutive 24 hour periods, affords effective LD night levels and thus reduces, alleviates or potentially eliminates nightly sleep disturbances and daytime sleepiness or drowsiness, and produces significantly high morning levels of LD. The high morning pre-dose LD blood plasma levels provided by the treatment regimen of the present invention alleviate or eliminate symptoms related to degenerative disorders of the central nervous system, Parkinson's disease in particular, motor skills, speech and related impairments, prior to the subsequent administration of the next day consecutive dose. In addition, the morning high LD blood plasma levels provided by the treatment regimen of the present invention allow a faster onset of the ON period and shorten the OFF period after the next day subsequent administration of the first dose. Moreover, the morning high LD blood plasma levels provided by the treatment regimen of the present invention result in better sleep quality throughout the night and alleviate or eliminate daytime sleepiness and drowsiness on the subsequent day.

In some embodiments, there is provided a use of an AP-CD/LD, administered to a patient in need thereof prior to going to sleep. Said bedtime, or nocturnal administration provides effective LD blood plasma levels throughout the night. In some embodiments, the dose should be administered no later than 3 hours apart from the last LD dose of the patient, but may be administered 1.25, 1.5, 1.75, 2.0, 2.25, 2.5, 2.75, 3.0, 3.25, 3.5, 3.75, 4.0, 4.25, 4.50, 4.75 or 5.0 hours from the administration of the last LD dose. In one aspect, the dose of levodopa in AP-CD/LD is about 250 mg. In another aspect, the dose of levodopa in AP-CD/LD is about 375 mg. In yet another aspect, the dose of levodopa in AP-CD/LD is about 500 mg. In some embodiments, the nocturnal administration of AP-CD/LD provides better sleep quality to the patient in need thereof. In other embodiments, the nocturnal administration alleviates or eliminates morning akinesia symptoms in patients in need thereof.

Levodopa is usually administered with a DOPA-decarboxylaze inhibitor, such as benserazide or carbidopa. Normally, levodopa is co-administered with carbidopa. The art discloses several effective carbidopa/levodopa combinations with different ratios between the two. There is much reasoning in favor of many ratios. Although there is a general consensus that the total daily dose of carbidopa should not exceed 150-200 mg, PD subjects are often treated with a vast variety of doses of LD that not always have the same carbidopa/levodopa ratio. Many patients, especially advanced PD patients, are prone therefore to reach the maximum allowed daily carbidopa amounts under current treatment schedules. In contrast, the treatment regimen of the present invention supplies carbidopa in sufficient quantity to provide a stable CD blood plasma concentration for 24 hour periods, regardless of the total LD daily dose administered according to the treatment regimen. Moreover, even with the supplementation of add-on dosages, the subject being treated according to the regimen of the invention will not exceed the maximum allowed daily carbidopa amounts, as the regimen provides effective amounts of carbidopa to inhibit peripheral decarboxylaze activity sufficiently over 24 hour periods. Studies show that peripheral DOPA decarboxylase is saturated by carbidopa at approximately 70 to 100 mg a day. Therefore in some preferred embodiments, the oral dosage forms administered according to the treatment regimen of the invention comprise carbidopa or pharmaceutically acceptable salt thereof, preferably in an amount from about 50 mg to about 75 mg of carbidopa each. Carbidopa is released from the dosage forms. In the treatment regimen of the present invention, the carbidopa released upon absorption provides blood plasma levels of carbidopa that are sufficient to adequately prevent peripheral LD side effects for consecutive 24 hour periods.

When designing a treatment regimen, it is compulsory that the doses of one dosing regimen be easily translated into another. It is well known in the art that some controlled-release dosage forms provide lower absolute bioavailability than immediate-release doses, and therefore also lower relative bioavailability in reference to the immediate release dose. This usually causes difficulties in transferring patients from one treatment to another, as individual responses in patients are often poorly predictable and one cannot lower bioavailability before trial and error. By providing stable LD blood plasma concentrations after repetitive dosing in a subject, the treatment regimen of the present invention affords a relative bioavailability which is not less than 95%, preferably not less than 90%, and even more preferably not less than 89%, 88%, 87%, 86%, or 85%. In preferred embodiments, the treatment regimen of the present invention provides an area under concentration-vs-time curve over 24 hour periods ($AUC_{0-24}$), and thus a relative bioavailability (F), which is not less than 95%, preferably not less than 90%, and even more preferably not less that 85%, of the relative bioavailability obtained with an equivalent dose regimen of immediate release dosage forms. Similarly, the treatment regimen of the present invention, after a single dose, provides an area under concentration-vs-time curve extrapolated to infinity ($AUC_{0-inf}$), and consequently, a relative bioavailability (F) which is not less than 89%, 88%, 87%, 86%, or 85% of the $AUC_{0-inf}$ obtained with an equivalent dose regimen of immediate release dosage forms.

In further aspect, the administration of said two doses is not restricted to specific alimentary requirements. Usually, Parkinson's disease patients are advised to avoid high-protein food, high acidity food and beverages, and are warned against delayed gastric emptying that might impede the action of conventional dosage forms of levodopa. Some levodopa products even advise taking the medicine on empty stomach. Once the number of doses to be administered is low, the restriction can be complied with. At higher dosing frequency, a patient may be required to fast for a significant portion of a day. Some dosage forms that can provide benefit at three and more times a day administration, require the medicine to be taken with a meal, sometimes a meal of no less than 750 kcal, whereof not less than 40% should be derived from fat. However, patients normally comply better with medications that do not require extensive fasting or purposeful excessive eating.

In the administration of said two dosages of levodopa according to the regimen of the present invention, a small meal may be recommended before the administration. No excessive restrictions on diet are imposed by said regimen, providing a significant advantage to the patient. In some embodiments, the meals to accompany the first dosing of the dosage forms have calorie value of below 550 kcal, preferably below 540 kcal, or below 530, 500, 450, 400, 350, 300, 250, 200, or 191 kcal. In preferred embodiments, the meal has calorie value of 191 kcal, with 49% of calories being derived from fat. In further embodiments, the meals to accompany the second dosing of the dosage forms have calorie value of ranging from about 430 kcal, to about 670 kcal, but can have the calorie value of 450, 475, 500, 525, 550, 575, 600, 625, 650 or 670 kcal. In further embodiments, the calorie value derived from fat, of said meal accompanying second administration of the regimen of the invention, comprise about 40%, or about 38%, 36%, 34%, 32%, or 30%. In further preferred embodiments, the amount fat in the meals is an average amount of fat in alimentary products for human consumption.

Whereas levodopa is used vastly and primarily for treatment of Parkinson's disease symptoms, there are conditions responsive to levodopa, such as restless leg syndrome and others, that are not directly related to Parkinson's disease. All the disadvantages of conventional regimens as disclosed above are valid for every other treatment of conditions, responsive to levodopa. The treatment of night symptoms remains a significant challenge. Therefore, in some embodiments, there is provided use of an accordion pill comprising levodopa for the treatment of symptoms responsive to levodopa in a subject in need thereof over nocturnal period. In further embodiments, the AP-CD/LD is administered to the subject at or before bedtime. In yet further embodiments, said administration provides improvement in sleep quality in said subject over the night following administration. In various embodiments, the dose of levodopa in the AP-CD/LD is about 250 mg, or about 375 mg, or about 500 mg. In other embodiments, there is provided use of AP-CD/LD for alleviating or eliminating the symptoms of morning akinesia or morning dystonia.

The present invention, thus generally described, will be understood more readily by reference to the following examples, which are provided by way of illustration and are not intended to be limiting of the present invention.

EXAMPLES

Example 1

Phase IIA Included 12 Early Stage PD Patients
Clinical Study Design:
A multi center, open, two-way randomized crossover, multiple dose, active control, pharmacokinetic study in Parkinson's patients that are not experiencing wearing off, treated with low dose AP-CD/LD
The group was crossed over with a daily equidose of immediate release (IR) preparations of carbidopa/levodopa.
The Objectives
The primary objective was to evaluate the blood level profile of the AP-CD/LD relative to that of IR carbidopa/levodopa.
Another objective was to monitor the subjects for adverse events during the study period and to compare the safety of the test products with the reference products.
The Course of the Study
Subjects were randomized to start with either AP-CD/LD or with IR-CD/LD. The AP-CD/LD was dosed at 0 and 8 hrs on each day, for seven days. The reference product was the commercially available 25/250 mg Dopicar® (Teva Pharmaceuticals) CD/LD immediate-release tablet (IR-CD/LD), which was administered four times a-day, as a ½ tablet (12.5/125) at 0, 4, 8 and 12 hours on each day, for seven days. Since the amount of CD from the IR-CD/LD was half of that given by the AP-CD/LD and below the recommended amount of daily CD (70-100 mg), additional CD was given with each dose during the pharmacokinetics (PK) evaluation day (day 7 of the control treatment period). On the PK day Patients were co-administered an additional 12.5 mg IR CD capsule with each Dopicar® dose to provide a total CD dose of 100 mg. The total daily CD/LD doses for both products were equivalent.

During days 1-6 of each period, the test and reference products were self-administered at home every day. On the 7th day of dosing in each period, patients were dosed in the clinic (PK day).

Within 7 days after the last PK day (days 15-22), the subjects underwent post-study medical evaluation including blood and urine testing.

Each group was crossed over with an equal-dose of IR levodopa in a randomized manner.

AP-CD/LD 50/250 mg, Carbidopa/Levodopa Dosage Form

| | Amount/AP-CD/LD (mg) | | |
|---|---|---|---|
| Component | Immediate Release Layer | Outer (sum of two films) | Internal layer Controlled release |
| Carbidopa | 25.0 | | 25.0 |
| Levodopa | 70.0 | | 180.0 |
| Eudragit S100 | | 47.1 | |
| Eudragit L100 | | 23.5 | 61.0 |
| Eudragit L100-55 | | 23.5 | |
| Fish Gelatin | | 94.2 | |
| Propylene glycol | | 94.2 | |
| KOH | | 6.0 | |
| Poloxamer 407 | | | 32.0 |
| PEG 400 | 3.1 | | 30.0 |
| Tween 80 | 11.8 | | |
| Povidone 90 | 13.7 | | |

Phase IIA, Subjects

| Subject number | Gender | Age | Duration of PD, (years) | Duration of LD's Treatment | | H&Y |
|---|---|---|---|---|---|---|
| 102 | M | 68 | 3 | 6 | months | 2 |
| 104 | M | 73 | 2 | 9 | months | 2 |
| 106 | M | 74 | 2 | 3 | months | 2 |
| 107 | M | 65 | 2 | 5 | months | 1.5 |
| 113 | M | 69 | 2 | 11 | months | 2 |
| 101 | M | 67 | 6 | 3 | years | 2 |
| 103 | M | 76 | 7 | 7 | years | 2 |
| 105 | M | 76 | 9 | 3 | years | 2 |
| 108 | M | 71 | 11 | 6 | years | 2 |
| 110 | M | 67 | 6 | 3 | years | 3 |
| 111 | M | 54 | 4 | 3 | years | 2 |
| 114 | M | 59 | 8 | 7 | months | 2 |

Results:

The results of primary objective (pharmacokinetic profile) are presented in FIG. 1. True controlled-release profile of LD has been accomplished. BID administration of AP-CD/LD provided 15 monitored hours coverage of 400-1,000 ng/ml LD plasma levels, and in fact 24 hours coverage profile, since significant morning levels were achieved.

BID administration of AP-CD/LD provided average plasma levels within the range that is currently obtained with four times a-day (equivalent total daily dose) LD formulation that is on the market, with substantially reduced peaks.

Morning starting plasma levels of LD from AP product were significantly higher than these from IR treatment (200 vs 30 ng/ml). This capability of AP-CD/LD can improve morning akinesia, improve sleep quality and reduce day time sleepiness.

Safety

No significant adverse effects were reported during the study.

Example 2

Phase IIB—12 Fluctuating PD Patients

The purpose of this study was to evaluate the efficacy (pharmacokinetics and pharmacodynamics) and the safety of AP-CD/LD 50/375 mg, in various groups of advanced PD patients, after multiple dosing, in comparison to CD/LD formulations, currently on the market.

Clinical Study Design

A multi center, open, two-way randomized crossover, multiple dose, active control, pharmacokinetic and pharmacodynamic study in patients with wearing off treated with high dose AP-CD/LD.

The group was crossed over with the patient's current treatment dose. The study was conducted in three medical centers.

The Objectives:

The primary objectives of the study was to evaluate the pharmacokinetic profile of AP-CD/LD relative to that of IR-CD/LD and to determine the relative pharmacodynamic profiles of the AP-CD/LD vs. IR-CD/LD under real conditions of use (i.e. derived from at-home diary entries). Another objective was to monitor the subjects for adverse events during the study period and to compare the safety of the test products with the reference products.

The secondary objectives of the study was to assess patient and investigator global evaluation of, and degree of satisfaction with, AP-CD/LD relative to IR-CD/LD; and to determine the pharmacodynamic profile of AP-CD/LD relative to that of IR-CD/LD during the PK day.

Pharmacodynamic Evaluation Methods:

ON/OFF chart on PK days by subject and investigator;

UPDRS Motor testing at baseline and at every hour until +16 hours on the PK days;

Self rating of ON/OFF by patient every ½ hour for 16 hours on days 4, 5 and 6 and on days 11, 12 and 13;

Total OFF time, total ON time, time to ON, Total time of On with non-troublesome dyskinesias and of ON with troublesome dyskinesias;

Other pharmacodynamic parameters were allowed to be calculated for exploratory evaluations.

Clinical Study Course

Days 1-6 and 8-13

Subjects were randomized to start with either AP-CD/LD or current treatment, taken for 6 days at home.

Subjects were asked to fill in an ON/OFF diary on days 4, 5 and 6 and on days 11, 12 and 13.

Dosing:

Test arm: BID administration of AP-CD/LD 50/375 mg (morning and +8 hours). Due to the individuality and variability of treatment of the fluctuating Parkinson's patient the subjects were allowed (if necessary) to take up to 3 daily add-on doses of IR-CD/LD on days 1-6 or 8-13 of the "at home" treatment. Each additional "add-on" doses was limited to either ½ tablet of Dopicar (12.5/125 mg CD/LD) or ¼ tablet of Dopicar (6.25/62.5 mg CD/LD). All add-on doses were documented in the subject's daily diary.

Control arm: The current, individual treatment of each subject.

No additional CD/LD was allowed after midnight of days 6 and 13 (prior to the PK day).

Days 7 and 14

Subjects were confined to the clinic from the previous night for the duration of the day until the next morning (36 hours).

Dosing:

Test arm: BID AP-CD/LD, No add-on doses were allowed during the PK day (during the blood sampling), since they will interfere with the pharmacokinetic profile. Additional IR-CD/LD was allowed only after the last blood sample was taken.

Control arm: 4×¾ tablet of Dopicar (18.75/187.5 mg CD/LD) at 0, +4, +8, +12 hours.

On day 7 (at the clinic), pharmacodynamic evaluations were conducted for the first 16 hours by an assessor using the UPDRS part III. The patient documented ON/OFF times for 16 hours. The objective of these UPDRS and ON/OFF evaluations on days 7 and 14 were to evaluate the pharmacokinetics/pharmacodynamic correlation. Each subgroup was crossed over with an equal-dose of current individualized levodopa treatment in a randomized manner.

Post Study Medical Evaluation:

Within 7 days after the last PK day (days 15-22), the subjects underwent post-study medical evaluation including blood and urine testing.

AP-CD/LD 50/375 mg, Designed for Advanced Stage PD Patients

| Component | Amount/AP-CD/LD (mg) | | | |
| --- | --- | --- | --- | --- |
| | Internal layer Controlled release | Outer (sum of two films) | Immediate Release capsule coating Layer | CD layer |
| Carbidopa | | | | 50 |
| Levodopa | 375 | | 50 | |
| Eudragit S100 | | 52 | | |
| Eudragit L100 | 80 | 26 | | |
| Eudragit L100-55 | | 26 | | 11 |
| Fish Gelatin | | 104 | | |
| Propylene glycol | | 104 | | |
| KOH | | 6.6 | | |
| Poloxamer 407 | 40 | | | 5.5 |
| PEG 400 | 40 | | 3 | |
| Titanium Oxide | | | 3 | |
| Kollidon VA64 | | | 15 | |

Results

Pharmacokinetics (PK)

Figure 2:
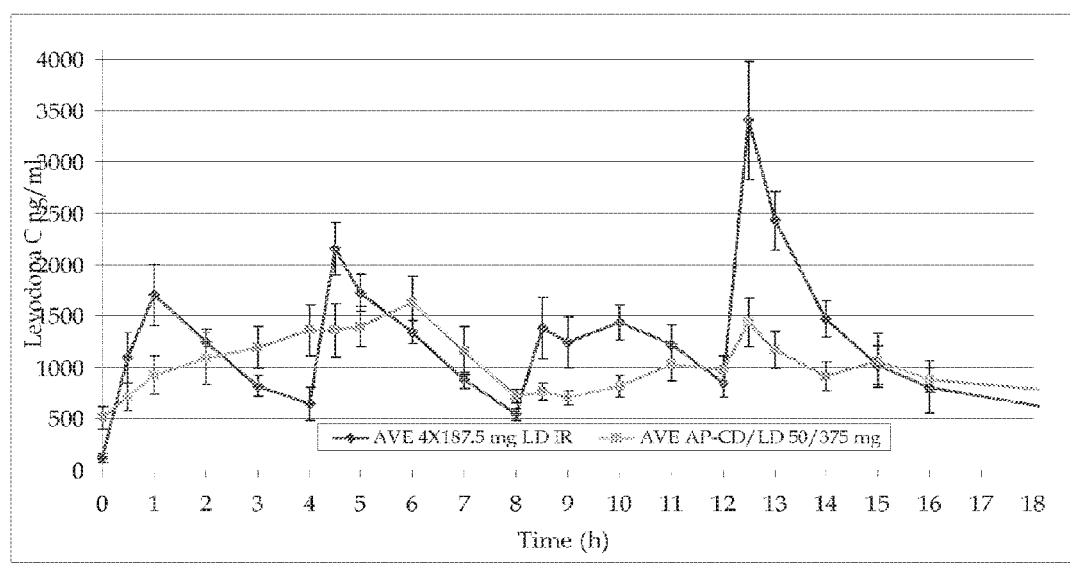
FIG. 2 presents the results of a pharmacokinetic equidose study in advanced PD patients with AP CD/LD 50/375 mg, administered b.i.d vs IR q.i.d.

Mean LD plasma concentrations are presented in FIG. 2.

True controlled-release profile of LD has been presented, with significantly more stable LD levels, during the 16 waking hours, and in fact 24 hours since significant morning levels were achieved.

A clear "flip-flop" kinetics (where Ka is much slower than Ke, hence the curve reflects the actual Ka) can be seen. LD's absorption phase was increased by 6 folds and more, by the AP-CD/LD. BID administration of AP-CD/LD provided 24 hours coverage of mean LD plasma levels of 522-1,710 ng/ml, in comparison to mean LD plasma levels of 91 (or 68—see below)-3,377 ng/ml, obtained with four times a-day administrations of IR-CD/LD, currently on the market (with equidose total daily LD of 750 mg, in both arms).

Peak to trough fluctuations (Mean Cmax–Mean Cmin) were statistically significantly reduced, by the AP-CD/LD, to a half. Similarly, peak to trough ratio (mean Cmax/mean Cmin) is reduced by almost sevenfold:

|  | Least-Squares Means[1] |  |  | Significance[3] |
| --- | --- | --- | --- | --- |
| LD Parameter | AP-CD/LD | Control | Ratio[2] | (p < 0.05) |
| Mean Cmax (ng/mL) | 2,285 | 3,999 | 0.571 | 0.0055 |
| Mean Cmin (ng/mL) | 348 | 90.9 | 3.830 | 0.0332 |
| Absolute Peak-to-Trough Fluctuation (ng/mL) | 1,937 | 3,908 | 0.496 | 0.0023 |
| Peak to trough ratio | 6.57 | 44.00 | 6.7 |  |

[1]Least-squares arithmetic means.
[2]Ratio calculated as AP-CD/LD least-squares mean divided by Control least-squares mean.
[3]Results of the statistical evaluation by ANOVA ($\alpha = 0.05$) for the hypothesis of equal treatment effects Mean $AUC_{0-24}$, achieved with the AP-CD/LD was 94.6% of the Mean $AUC_{0-24}$ achieved by IR-CD/LD. This calculation is based on the assumption that LD level at t=24 h is equal to LD level at t=0, in both arms (whereas current available controlled release LD products decrease bioavailability to about 75%).

The LD morning plasma levels achieved with the AP-CD/LD are statistically significantly higher (p=0.0191) than those achieved with the commercial IR treatment: 522 ng/ml vs. 91 ng/ml.

Pharmacodynamics

In 10 patients who completed the study in accordance with the study protocol, a statistically significant decrease in 'OFF time' and statistically significant reduction in the number of doses per day were achieved. In 80% of these patients, an average reduction of about 35% in the OFF time (2.96 hours compared to 4.48 hours with their current treatment) was achieved, which is statistically significant.

The number of daily doses in this patient group was reduced by half, from 6.0 times per day to 3.2 times per day (namely—BID administration of AP-CD/LD plus 1.2 add-on doses per day), with a statistically significance. This reduction was obtained due to an effective long acting AP-CD/LD. This achievement addresses one of the current unmet needs with respect to PD treatment—the daily significant pill burden, which is a result of the very short half-life of LDs preparations currently on the market.

Both subjects' and investigators' CGI and GSS evaluations correlated with the improvements demonstrated in the various pharmacodynamics end-points.

Mean Time to ON after First Dose (Day 7)
Mean Time to ON (Hours) Post Morning Dose on Day 7 (N=6)

|  | AP-CD/LD | Current | Difference |
| --- | --- | --- | --- |
| Mean Time to ON Post Morning Dose | 0.64 | 0.97 | −0.33 |

The shorter Mean Time to On, with AP-CD/LD, was obtained due to two attributes:

Significantly higher LD plasma levels at time 0 (7 AM), due to the true-controlled release performances of the AP-CD/LDs given the day before (522.0 vs 90.9 ng/ml, as described above);

An efficient IR component of the AP-CD/LD.

The significantly higher morning LD plasma levels provide a very important advantage in the treatment of advanced-stage PD patients.

PK/PD Correlation (Day 7)

Figure 5:
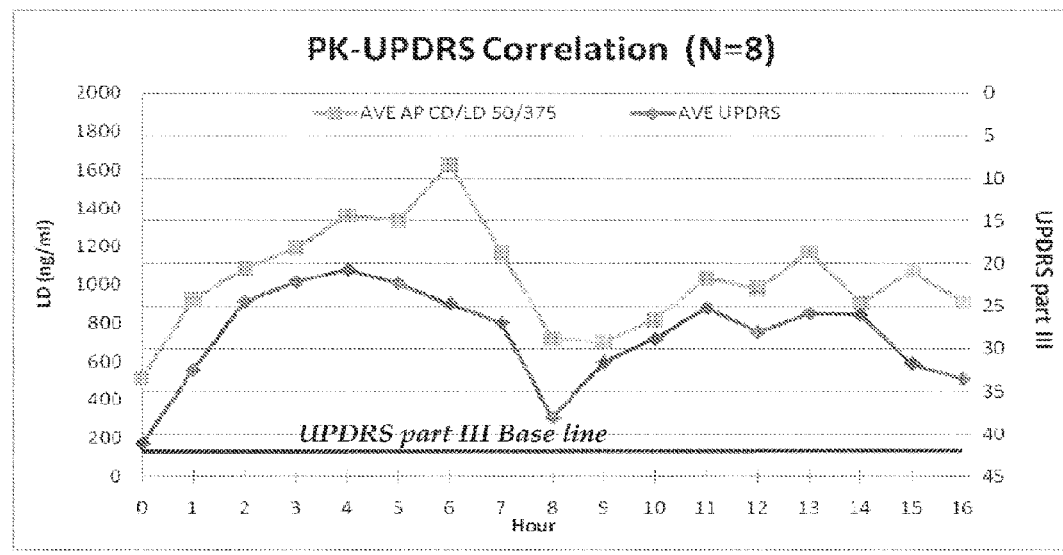
FIG. 5 presents strong correlation between steady LD blood plasma levels and elevated UPDRS scores of the patients—AP-CD/LD—50/375 mg.

A strong correlation was demonstrated in day 7 between LD plasma levels and ON/OFF and UPDRS data, during the 16 hours' evaluations. This validates the concept of the strong PK/PD correlation in LD treatment, with respect to the drug's motor complications, as well as the huge importance of stabilizing the drug's PK. The graph, presenting the correlation of UPDRS score with the blood plasma levels of LD is presented in FIG. 5. As can be seen from the figure, the UPDRS does not go above the baseline score, meaning steady improvement in PD symptoms over tested period.

Safety

No significant adverse effects were reported during the study.

Subjects Enrolled:

| Randomization No. | Gender | Age | Duration of PD, (years) | Duration of LD's Treatment, (years) | H&Y | Usual Daily Current LD Treatment* |
| --- | --- | --- | --- | --- | --- | --- |
| 301 | F | 61 | 19 | 16 | 2.5 | Completed the study not per protocol |
| 303 | M | 75 | 10 | 6 | 2.5 | 5 × 125 + 100 = 725 mg |
| 304 | M | 77 | 10 | 10 | 2.5 | 5 × 125 = 625 mg |
| 305 | M | 84** | 12 | 10 | 3 | 4 × 125 + 3 × 100 + 62.5 = 862.5 mg |
| 306 | M | 62 | 6 | 6 | 2 | 5 × 125 = 625 mg |
| 307 | M | 60 | 11 | 9 | 3 | 200 + 8 × 100 = 1,000 mg** |
| 308 | M | 71 | 17 | 15 | 2.5 | 5 × 125 = 625 mg |
| 309 | F | 61 |  |  |  | Dropped out |
| 310 | F | 57 | 13 | 13 | 3 | 6 × 125 = 750 mg |
| 311 | M | 77 | 9 | 6 | 2.5 | 5 × 125 = 625 mg |
| 312 | M | 64 | 10 | 6 | 2 | 6 × 125 = 750 mg |
| 313 | M | 61 | 8 | 6 | 2.5 | 5 × 187.5 = 937.5 mg |

*Subject's usual LD treatment, in addition to other medications. This was also the control arm's treatment in days 4-6 and 11-13, for each subject, in general.
**Both deviations above were pre-approved by the IRB.

Based on examples 1 and 2, the AP-CD/LD has demonstrated its potential to a significantly improve LD treatment through:

Reducing the pills burden;
Decreasing wearing OFF;
Improving patients' compliance with therapy; and
Improving sleep quality and morning akinesia.

Example 3

Pharmacodynamic Evaluation in Fluctuating Patients

The purpose of this study was to evaluate pharmacodynamic changes in fluctuating PD patients upon treatment with AP-CD/LD 50/375 mg, following three weeks treatment.

Study Objectives:

Primary objectives of the study were to evaluate a change in the total daily OFF time (hr) from at home ON/OFF diaries, at week 3 of each treatment, between AP-CD/LD and active control; and to assess patient and investigator global evaluation, and degree of satisfaction with, AP-CD/LD relative to current levodopa treatment.

Course of the Study:

The study included multiple dosing for 21 days with the AP-CD/LD crossed over with a similar duration of treatment with the patient's current therapy. Both treatment periods included 21 days of treatment out of which the first 14 days were for equilibration (readjusting to the treatment after the crossover) and the last 4 days were for the evaluation (test period).

Subjects were randomized to start with either AP-CD/LD or current treatments. There was no washout period between treatment periods due to the equilibration period prior to the test periods. The test period included 4 days of treatment. Pharmacodynamics evaluation was based on ON/OFF home diaries from 3 days prior to the clinic visit and on UPDRS part III performed every hour for 6 hours during a clinic visit on the last day of each test period (days 21 and 42).

Results

In a sub-group of 6 patients the regimen was based on BID AP CD/LD 50/375 mg. In this group the Total OFF Time was reduced from 2.9 hours with the current treatment to 1.2 hours with the AP treatment. In addition, a significant reduction (more than threefold) of LD doses was achieved. The number of LD daily doses in their current treatment arm was 6.6 times a day.

Example 4

Pharmacokinetic Profile of AP-CD/LD 50/500 mg

The purpose of the study was to evaluate the pharmacokinetic parameters of AP-CD/LD 50/500 mg, in healthy volunteers, as single dose versus IR of 2×250 mg LD (Sinemet® 25/250 mg (Merck & Co., Inc.)).

Study Objectives:

The primary objective was to compare the pharmacokinetic profiles of LD and carbidopa, following oral administration of a single-dose of a controlled-release gastric retentive formulations, with that obtained following oral ingestion of two consecutive doses of the reference product Sinemet®, taken after a low-medium calorie meal.

The secondary objective was to monitor the subjects for adverse events during the study period and to compare the safety of the test formulation with the reference product.

Study Design:

Single center, randomized, single-dose, open label, two-way, comparative crossover study. The wash-out period between study sessions will be at least 7 days.

Course of the Study:

Pretreatment—50 mg of carbidopa three times daily on the three days prior to each drug administration was administered to diminish or avoid the ADRs that were anticipated in LD-naïve patients.

Dosing—the dosing of either 2×Sinemet® 25/250 mg or 1×AP-CD/LD 50/500 mg was performed in a cross-over manner with washout period of 1 week.

Formulation of AP-CD/LD 50/500 mg

| | Amount/AP-CD/LD (mg) | | | |
|---|---|---|---|---|
| Component | Internal layer Controlled release | Outer (sum of two films) | Immediate Release Levodopa Layer | CD layer |
| Carbidopa | | | | 50 |
| Levodopa | 430.0 | | 70.0 | |
| Eudragit S100 | 14.3 | 50.9 | | |
| Eudragit L100 | 109.9 | | | |
| Eudragit L100-55 | | | 12.7 | 11 |
| Fish Gelatin | | 50.9 | | |
| Polyox WSR-205 | | 5.9 | | |
| KOH | | 2.1 | | |
| Poloxamer 407 | | | 9.5 | 5.5 |
| Poloxamer 124 | 62.1 | 14.9 | | |
| PEG 400 | 62.1 | 35.7 | | |
| Sodium Starch Glycolate | | | 50.0 | |

Figure 3:
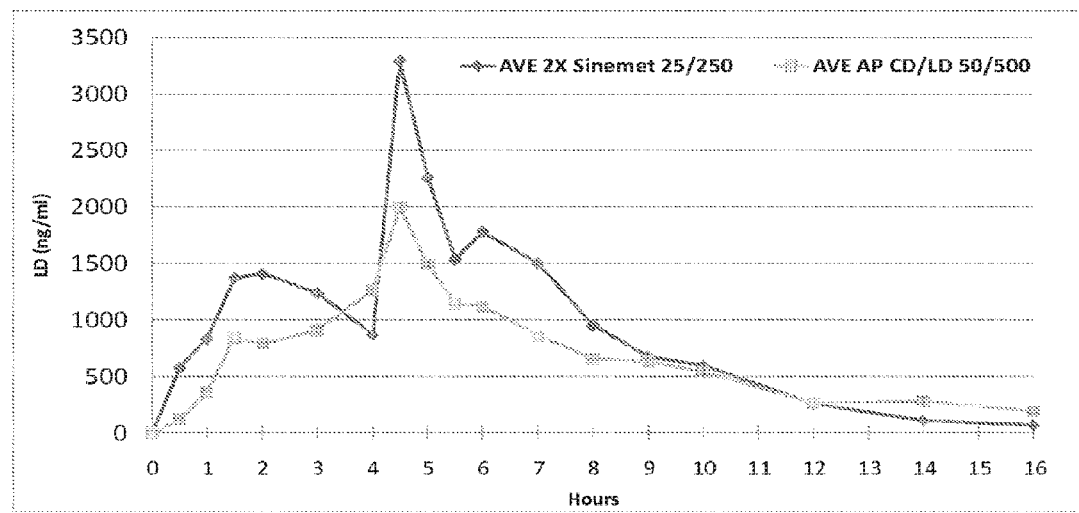
FIG. 3 presents the results of a pharmacokinetic equidose study in healthy volunteers with AP CD/LD 50/500 mg, administered qd (once) vs IR b.i.d.

Results:

The pharmacokinetic profile is presented in FIG. 3.
The PK parameters are summarized in table below:

| | Least-Squares Means [1] | | | 90% Confidence Interval [3] | |
|---|---|---|---|---|---|
| Parameter | Test | Reference | Ratio [2] | Lower | Upper |
| AUG 0-t (ng-hr/mL) | 10693 | 14047 | 0.761* | 0.615 | 0.907 |
| AUCinf (ng-hr/mL) | 12426 | 14123 | 0.880 | 0.486 | 1.274 |
| Cmax (ng/mL) | 1951 | 4062 | 0.480* | 0.153 | 0.808 |
| Tmax (hour) | 4.67 | 4.83 | 0.966 | — | — |
| Ke (1/hour) | 0.2829 | 0.4041 | 0.700 | — | — |
| T½ (hour) | 5.15 | 1.76 | 2.927 | — | — |

[1] Least-squares geometric means for ln-transformed data.
[2] Ratio calculated as Test least-squares mean divided by the Reference least-squares mean.
[3] Confidence interval on the ratio.
*Comparison was detected as statistically significant by ANOVA ($\alpha = 0.05$).

The results show that high LD concentrations can be reached with AP-CD/LD 50/500 mg, concentrations sufficient to provide the need for advanced PD patients.

Example 5

Typical Exemplary Menu Employed in the Examples Above
Version 1
  Breakfast (−30 min) 529 Kcal 51% fat
  2 slices of bread, butter (40 g), 8 olives, cookies (40 g), tea (decaffeinated, 1 spoon of sugar).
  Lunch (+5 hours) 530 Kcal 40% fat
  Salami sandwich (one, approx. 50 g), vegetable salad (120 g), fruit salad (1 cup)
  Snack (+7.75 hours) 190 kcal 49% fat
  Plain croissant (50 g)
  Dinner (+12 hours) 525 kcal 34% fat
  Fried breaded chicken breast (100 g), vegetable salad (120 g), rice (1 cup)
Version 2
  Breakfast (−30 min) 529 Kcal 51% fat
  2 slices of bread, butter (40 g), 8 olives, cookies (40 g), tea (decaffeinated, 1 spoon of sugar).
  Lunch (+5 hours) 648-670 Kcal 34% fat
  Option 1: Salami sandwiches (two, approx. 100 g), vegetable salad (120 g), fruit salad (1 cup)
  Option 2: Humus sandwiches (two, approx. 100 g), vegetable salad (120 g), fruit salad (1 cup)
  Snack (+7.75 hours) 190 kcal 49% fat
  Plain croissant (50 g)
  Dinner (+12 hours) 525 kcal 34% fat
  Fried breaded chicken breast (100 g), vegetable salad (120 g), rice (1 cup)
Version 3
  Snack at arrival 190 kcal 49% fat
  Plain croissant or cookies (50 g), non-caffeinated tea
  Lunch (~+5 hours) 648-670 Kcal 34% fat
  Option 1: Salami sandwiches (two, approx. 100 g), vegetable salad (120 g), fruit salad (1 cup)
  Option 2: Humus sandwiches (two, approx. 100 g), vegetable salad (120 g), fruit salad (1 cup)
  Snack prior to second dosing of AP 190 kcal 49% fat
  Plain croissant (50 g) or cookies, non-caffeinated tea
Version 4
  Breakfast (−30 min) 529 Kcal 51% fat
  Option 1: 2 slices of bread with butter (40 g) with 1 small Plain croissant
  Option 2: 2 slices of bread with butter (40 g) with Vanilla pudding
  Both with tea (decaffeinated, 1 spoon of sugar)
  Lunch (~+5 hours) 648-670 Kcal 34% fat
  Option 1: Salami sandwiches (two, approx. 100 g), vegetable salad (120 g), fruit salad (1 cup)
  Option 2: Humus sandwiches (two, approx. 100 g), vegetable salad (120 g), fruit salad (1 cup)
Throughout the Day (Optional)
Cookies and Non-Caffeinated Tea Those of skill in the art will recognize that numerous modifications and changes may be made to the exemplary designs and embodiments described herein and that the invention is not limited to such embodiments.

The invention claimed is:

1. A method for the treatment of symptoms of Parkinson's disease in a subject in need thereof, comprising:
   repetitively administering to the subject, over a period of more than one week, an accordion pill comprising a therapeutically effective amount of levodopa, in a twice-a-day administration regimen having a first dose of the day and a second dose of the same day, wherein the second dose of each day is administered about 8 to about 10 hours after the first dose of that day, with the first dose of the following consecutive day commencing about 24 hours after the first dose of the previous day,
   wherein the accordion pill comprising levodopa is a multilayered gastroretentive dosage form, folded into a capsule in undulated form, which unfolds upon contact with gastric fluids.

2. The method according to claim 1, wherein the accordion pill comprises about 250 mg levodopa, and wherein the repetitive twice daily administration regimen provides average blood plasma levels of levodopa of 200-1,000 ng/ml in the subject over a 24 hour period following administration of the first dose of the day; or
   wherein the accordion pill comprises about 375 mg levodopa, and wherein the repetitive twice daily administration regimen provides average blood plasma levels of levodopa of 500-1,500 ng/ml in the subject over a 24 hour period following administration of the first dose of the day; or
   wherein the accordion pill comprises about 500 mg levodopa, and wherein the repetitive twice daily administration regimen provides average blood plasma levels of levodopa of 700-2,000 ng/ml in the subject over a 24 hour period following administration of the first dose of the day.

3. The method according to claim 2, wherein the accordion pill comprises about 375 mg levodopa, and wherein the repetitive twice daily administration regimen provides an average blood plasma level of levodopa of 500-1,500 ng/ml in the subject over a 24 hour period following administration of the first dose of the day.

4. The method according to claim 2, wherein the accordion pill comprises about 375 mg levodopa, and wherein the twice daily administration regimen after multiple administrations provides an average blood plasma level of levodopa of 500-1,500 ng/ml in the subject over a 24 hour period following administration of the first dose, and wherein the repetitive twice daily administration regimen reduces total OFF time during waking hours of not less than 50% in comparison to the total OFF time associated with immediate-release formulations comprising daily equal-doses of levodopa, administered four times a day.

5. The method according to claim 1, wherein the accordion pill provides absorption of levodopa into the blood plasma of the subject for about 6 to about 14 hours following administration of the accordion pill to the subject.

6. The method according to claim 1, wherein the repetitive twice daily administration regimen further comprises administering to the subject one or more dosage forms comprising immediate-release or controlled-release levodopa.

7. The method according to claim 1, wherein the repetitive twice daily administration regimen provides stable blood plasma levels of levodopa with an absolute peak-to-trough ratio of levodopa blood plasma concentrations below 7.

8. The method according to claim 1, wherein the repetitive twice daily administration regimen reduces peak-to-trough fluctuations in the blood plasma levels of levodopa in the subject by at least 50% in comparison to immediate-release formulations of levodopa comprising daily equal-doses, administered four times a day.

9. The method according to claim 1, wherein the repetitive twice daily administration regimen shortens or eliminates total OFF time during waking hours in the subject.

10. The method according to claim 9, wherein the repetitive twice daily administration regimen further comprises administering to the subject one or more add-on dosage forms comprising immediate-release or controlled-release levodopa.

11. The method according to claim 1, wherein the repetitive twice daily administration regimen allows faster onset of the ON period in the subject.

12. The method according to claim 1, wherein the repetitive twice daily administration regimen alleviates or eliminates nightly sleep disturbances and daytime sleepiness or drowsiness in the subject.

13. The method according to claim 1, wherein the repetitive twice daily administration regimen produces significantly high morning levels of levodopa in the blood plasma of the subject, thereby allowing faster onset of the ON period or shortening of the OFF period after the first dose of the day.

14. The method according to claim 13, wherein the repetitive twice daily administration regimen alleviates or eliminates nightly sleep disturbances and daytime sleepiness or drowsiness in the subject.

15. The method according to claim 1, wherein the accordion pill further comprises an amount of carbidopa sufficient to provide carbidopa blood plasma levels sufficient to adequately prevent peripheral levodopa side effects in the subject.

16. The method according to claim 15, wherein the accordion pill comprises about 250 mg levodopa and 50 mg of carbidopa, and wherein the repetitive twice daily administration regimen provides an average blood plasma level of levodopa of 200-1,000 ng/ml in the subject over a 24 hour period following administration of the first dose of the day; or wherein the accordion pill comprises about 375 mg levodopa and 50 mg of carbidopa, and wherein the repetitive twice daily administration regimen provides an average blood plasma level of levodopa of 500-1,500 ng/ml in the subject over a 24 hour period following administration of the first dose of the day; or wherein the accordion pill comprises about 500 mg levodopa and 50 mg of carbidopa, and wherein the repetitive twice daily administration regimen provides an average blood plasma level of levodopa of 700-2,000 ng/ml in the subject over a 24 hour period following administration of the first dose of the day.

17. The method according to claim 15, wherein the accordion pill comprises about 50 mg to about 75 mg of carbidopa.

18. The method according to claim 1, wherein the repetitive twice daily administration regimen provides stable blood plasma levels of levodopa in the subject with values of area-under-the-curve over 24 hours and a relative bioavailability that is not less than 85% relative to the values obtained from immediate-release formulations comprising daily equal-doses administered four times a day.

* * * * *